(12) United States Patent
Bamberg et al.

(10) Patent No.: US 7,743,639 B2
(45) Date of Patent: Jun. 29, 2010

(54) METHOD, DEVICE, AND TEST SPECIMEN FOR TESTING A PART, AND USE OF THE METHOD AND DEVICE

(75) Inventors: Joachim Bamberg, Dachau (DE); Wolf-Dieter Feist, Vierkirchen (DE)

(73) Assignee: MTU Aero Engines GmbH, Munich (DE)

( * ) Notice: Subject to any disclaimer, the term of this patent is extended or adjusted under 35 U.S.C. 154(b) by 293 days.

(21) Appl. No.: 10/581,539

(22) PCT Filed: Nov. 9, 2004

(86) PCT No.: PCT/DE2004/002473

§ 371 (c)(1),
(2), (4) Date: Apr. 12, 2007

(87) PCT Pub. No.: WO2005/054841

PCT Pub. Date: Jun. 16, 2005

(65) Prior Publication Data

US 2007/0256473 A1    Nov. 8, 2007

(30) Foreign Application Priority Data

Dec. 2, 2003    (DE) ............................... 103 56 223

(51) Int. Cl.
  *G01N 29/00* (2006.01)
(52) U.S. Cl. ....................................... 73/1.86
(58) Field of Classification Search ................. 73/1.82, 73/1.86, 598, 600, 606
  See application file for complete search history.

(56) References Cited

U.S. PATENT DOCUMENTS

| | | | | |
|---|---|---|---|---|
| 3,933,026 A | * | 1/1976 | Ham et al. | ..................... 73/1.86 |
| 4,173,139 A | * | 11/1979 | Conn | .......................... 73/1.84 |
| 4,203,315 A | * | 5/1980 | Vieu et al. | .................... 73/1.86 |
| 4,747,295 A | | 5/1988 | Feist et al. | .................... 73/1.86 |
| 4,963,826 A | * | 10/1990 | Capobianco et al. | ........ 324/202 |
| 5,337,611 A | * | 8/1994 | Fleming et al. | ............... 73/622 |
| 5,670,719 A | | 9/1997 | Madsen et al. | ................. 73/619 |
| 5,952,577 A | * | 9/1999 | Passi | ........................... 73/618 |
| 7,434,468 B2 | * | 10/2008 | Puckett | ........................ 73/649 |
| 2003/0078681 A1 | * | 4/2003 | Dubois et al. | .................. 700/31 |

FOREIGN PATENT DOCUMENTS

| | | |
|---|---|---|
| DE | 34 25 263 | 1/1985 |
| DE | 44 07 547 | 9/1995 |
| DE | 199 25 801 | 12/2000 |
| DE | 100 15 702 | 10/2001 |
| EP | 0 743 128 | 11/1996 |
| JP | 7-76167 | 3/1995 |
| JP | 7-229878 | 8/1995 |
| JP | 2002-48773 | 2/2002 |
| JP | 2002-328098 | 11/2002 |
| JP | 2002328098 A | * 11/2002 |

OTHER PUBLICATIONS

Patent Abstracts of Japan, vol. 2003, No. 03, May 5, 2003.
Patent Abstracts of Japan, vol. 1995, No. 06, Jul. 31, 1995.
Patent Abstracts of Japan, vol. 2002, No. 06, Jun. 4, 2002.
Patent Abstracts of Japan, vol. 1995, No. 11, Dec. 26, 1995.
International Search Report, PCT International Patent Application No. PCT/DE2004/002473, Apr. 1, 2005 (translated).
Written Opinion of the International Searching Authority, PCT International Patent Application No. PCT/DE2004/002473, Apr. 1, 2005 (translation of Supplemental Sheets provided).

* cited by examiner

*Primary Examiner*—Hezron Williams
*Assistant Examiner*—Tamiko D Bellamy
(74) *Attorney, Agent, or Firm*—Kenyon & Kenyon LLP

(57) ABSTRACT

A method and a device are for testing the detectability of at least one flaw in a component, or for evaluating ultrasonic signals of the flaw. The method provides for an electronic specification of the flaw to be generated, which includes a two-dimensional or three-dimensional point pattern. This specification predefines the number, position, shape, orientation, and dimensions of flaws to be deliberately generated. A test specimen is produced, where for each point of the point pattern, a microcrack is generated at the position of this point. An ultrasonic image of the test specimen is recorded and evaluated. The test specimen may be made out of a material transparent to visible light, e.g., crown glass, optical glass, borosilicate glass, or quartz glass. The microcracks may be produced, using internal laser engraving.

17 Claims, No Drawings

METHOD, DEVICE, AND TEST SPECIMEN FOR TESTING A PART, AND USE OF THE METHOD AND DEVICE

FIELD OF THE INVENTION

The present invention relates to a method and a device for testing the detectability of at least one flaw in a component, or for evaluating an ultrasonic signal of the flaw as well as a test specimen for implementing the method.

BACKGROUND INFORMATION

The metallic materials used for manufacturing heavy-duty components must satisfy stringent quality standards. Such components include, for example, rapidly rotating disks of turbine or compressor stages of a gas turbine that propels an airplane. Blades are attached to these disks. In such a material, flaws may occur that are caused by, in particular, the manufacturing process of the material. These flaws include casting bubbles, pores, inclusions, heat-treatment cracks, and welding cracks. Methods and devices are needed for detecting such flaws and quantifying the detectability of flaws.

The use of ultrasonics for non-destructive material testing is described in "Dubbel—Taschenbuch für den Maschinenbau" (Dubell—Pocket Book of Mechanical Engineering), 20th edition, Springer Publishing House, 2001, E33 and S87.

Test specimens and calibration specimens are used for the reliable and comparable testing of a component with the aid of ultrasonics. Conventionally, blocks having flat-top bores or cross bores are provided for this. These blocks are mostly made out of the same material as the part to be manufactured. Therefore, neither the shape and dimensions, nor the reflection characteristic and reradiation characteristic of real flaws are realistically described.

Japanese Published Patent Application No. 2002-048773 describes a device for calibrating an ultrasonic testing device. The method may be used for a testing device having one probe and for one having two probes. Several calibration holes are introduced into a welded component in a particular manner. The probe(s) are applied or attached to the part and at specific angles to one another, and a characteristic curve for the distance, spacing or interval between distance and amplitude is generated.

In U.S. Pat. No. 5,670,719, a system is described which ascertains the resolution of medical ultrasonic testing devices. The system predicts the local wounds or tumors in the tissue of a human that the testing device detects. A phantom container simulates human tissue. Wounds and tumors are simulated in several layers with the aid of scattering particles. It is determined, which particles are detected and which are not.

SUMMARY

Example embodiments of the present invention may provide a reliable method and a reliable device for testing the detectability and evaluating the shape, position, size, and orientation of flaws in a component.

According to an example embodiment of the present invention, a method includes the following steps:

An electronic specification of at least one flaw is generated. The specification stipulates the position, shape, size, and orientation of the flaw or flaws. It includes a three-dimensional point pattern of the flaw or flaws and defines, in this manner, the position of each point of the point pattern in a three-dimensional space.

A test specimen is produced according to the specification. In this connection, for each point of the point pattern, a microcrack in the test specimen is produced at the position of this point, and therefore, a microcrack field representing the flaw is produced.

Ultrasonic signals of the test specimen are recorded. Any ultrasonic method may be used for this. The ultrasonic signal is analyzed, for example, in the form of images generated from the signals. The evaluation of the ultrasonic signals includes at least the test of whether or not the deliberately produced flaw is detectable in the image. During the evaluation of flaws, the ultrasonic signals are assigned to the different flaws, in order to deduce the shape/type of the flaw from the signals in the case of real measurements on components.

The method may provide a manner of inexpensively selecting an arbitrary flaw and testing if this flaw is detected. In addition, the method may provide a manner to render visible how flaws manifest themselves in an ultrasonic signal of the component. Any number of flaws may be selected or specified reliably and highly realistically with regard to size, shape, and position. After the signal is evaluated, the flaws that are detected and the flaws that are not detected may be quantitatively specified. This may allow the method to reliably specify the real flaws, microstructures, and/or textures that may be detected in a component and the ones that may not. Since the method may allow the detectability of flaws to be specified, e.g., with regard to size, shape, and position, the potential rigidity or strength of the material may be reliably utilized in the design and manufacture of the component, where neither flaws remain undetected, nor the component is overdimensioned and, therefore, the material apportioned too generously.

Realistic test cases may be rapidly produced, with the aid of which it is possible to select a complete spectrum of test cases. The produced flaws are generated such that they come close to real flaws with regard to shape, reflective behavior, and reradiation or backscattering characteristic.

The method may also be used for testing or ascertaining the resolution of an ultrasonic testing system. Through use of the method, it may be tested whether or not the ultrasonic testing system used for recording the image detects the purposefully generated flaws. It is possible to obtain information about the test sensitivity as a function of the dimensions, shape, and position of the flaws. This may allow the method to test and guarantee a particular ultrasonic testing technology. For example, the applicability of a new ultrasonic testing technique may be tested. The method may allow one to verify the resolution of the testing system (device, cable, converter) or testing method, which is used in the production of heavy-duty components. Such a verification may be necessary, for example, for certifying rotating blades or disks for airplane engines and may be provided with the aid of the method.

The material, of which the test specimen is made, is not necessarily the same material that is intended or used for manufacturing the component. The method may allow a material for the manufacture of the test specimen to be selected so that the microcracks in it may be produced simply or inexpensively. The test-specimen material does not have to withstand the same loads as the one intended for the component. The latter may be high-strength steel, and from a standpoint of production engineering, it may be difficult and expensive to deliberately produce flaws in this steel. Thus, the method may provide a manner of reducing costs. A material, which is less expensive or more suitable for the deliberate production of flaws than the one provided for the component, may be used for the test specimen.

The microcracks may be generated, using internal laser engraving. The generation of microcracks with the aid of internal laser engraving is described in German Published Patent Application No. 34 25 263, German Published Patent Application No. 44 07 547, German Published Patent Application No. 100 15 702 and German Published Patent Application No. 199 25 801. The microcracks may be generated particularly easily and rapidly with the aid of internal laser engraving. Through specific stipulation of parameters of the method for internal laser engraving, the microcracks may be generated precisely in predefined sizes in a microcrack field of predefined shape, size, and orientation.

The microcracks may be generated such that their largest dimension is smaller than the wavelength used for recording the ultrasonic image. In this manner, the shape of an individual microcrack is no longer discreetly reproduced. The flaw and its reflective behavior is only produced by the combination of microcracks, which is stipulated by the specification. This allows the shape and the dimensions of the deliberately generated flaw to be precisely specified, without the dimension of the microcracks influencing the result of the method. Which flaws are detected and which are not detected, is a function of the number and distribution of the points in the point pattern.

The material intended for the component and the material from which the test specimen is manufactured may have approximately the same elastic parameters. This may allow the method to attain a particularly high degree of realism. If the method is used for ascertaining the resolution of the ultrasonic testing system, then the result is that the resolution of an ultrasonic testing system in the test-specimen material comes particularly close to that in the component material.

DETAILED DESCRIPTION

In the following, example embodiments of the present invention are described. In an exemplary embodiment, a disk, which rotates rapidly in a turbine stage of a turbojet engine, and to which turbine blades are attached, acts as a component. This disk may be made out of a heavy-duty, nickel-based alloy. It may be expensive and time-consuming to make a test specimen out of this material and deliberately produce flaws in this test specimen, and in addition, it may not be possible in all of the desired positions and orientations. On the other hand, the test specimen may be made in almost any shape, out of a material, whose acoustic characteristics are similar to those of the component material, and which is transparent to light, and test flaws may be produced in almost any size, shape, and orientation.

With the aid of an ultrasonic testing system, a plurality of ultrasonic signals of the test specimen is recorded. The resolution of an ultrasonic testing system is a function of the angle between the propagation direction of the ultrasound and the direction of the largest dimension of a flaw in the test specimen, and/or a function of the angle between the propagation direction and the surface of the test specimen. Thus, several ultrasonic signals of the test specimen are generated from different directions.

The method may be used for ascertaining the resolution of an ultrasonic testing system, based on the material provided for the component. For this purpose, several specifications are successively generated from microcracks. The specifications differ from each other such that each point pattern of a specification has a smaller maximum dimension than all of the preceding specifications. For each specification, a test specimen is produced according to the specification, and ultrasonic signals of this test specimen are generated by the ultrasonic testing system. It is checked whether or not the device detects a flaw in the test specimen. The method is interrupted when the testing device does not detect any flaw in the test specimen, which was manufactured according to the specification generated last. In this case, several signals may be generated from different angles, as well. The maximum dimension of the smallest detected flaw is used as a measure of the resolution of the testing system.

In addition, the method may also be used for producing a library of possible flaws in the component. A number of possible flaws are specified or selected, each flaw being stipulated by a specification via a point pattern. For every possible flaw, with the aid of the method:

on one hand, a test specimen in which the flaw is purposefully achieved is produced, and on the other hand, ultrasonic signals of this test specimen are generated.

An image of the test specimen and the ultrasonic signals of the corresponding test specimen are recorded for each flaw. Through evaluation of the signals, it is ascertained if the flaw is detectable in at least one of the ultrasonic signals. In addition, the number, shape, position or attitude, and position of the flaws detected in the ultrasonic signal may be compared to the specification and/or to the flaws deliberately produced in the test specimen.

The library may make it easier to evaluate ultrasonic signals of a manufactured component and to make conclusions from the ultrasonic signals of the component, regarding the presence and the type, position, and dimension of flaws in the component.

What is claimed is:

1. A method for at least one of (a) testing detectability of at least one flaw in a component and (b) evaluating ultrasonic signals of the flaw, comprising:

generating an electronic specification of the flaw, the electronic specification including at least one of (a) a two-dimensional and (b) a three-dimensional point pattern;

after the generating, manufacturing a test specimen, for each point of the point pattern, a microcrack in the test specimen generated at a corresponding position to form a microcrack field representing the flaw; and recording and evaluating ultrasonic signals of the test specimen.

2. The method according to claim 1, wherein the microcracks are produced in the manufacturing step by internal laser engraving.

3. The method according to claim 1, wherein a largest dimension of the microcracks is smaller than a wavelength used for recording the ultrasonic signals in the recording step.

4. The method according to claim 1, wherein the test specimen is manufactured in the manufacturing step of a material transparent to visible light.

5. The method according to claim 4, wherein the transparent material includes at least one of (a) crown glass, (b) optical glass, (c) borosilicate glass and (d) quartz glass.

6. The method according to claim 1, wherein a material of the test specimen has approximately same elastic parameters as a material of the component.

7. The method according to claim 1, wherein the generating step includes generating several specifications having one point pattern each, the point patterns differing with regard to at least one of (a) size, (b) shape and (c) orientation, and for each specification:

the manufacturing of a test specimen being performed in accordance with a corresponding specification; and the recording and evaluation of ultrasonic signals of the corresponding test specimen being performed.

8. A method for at least one of (a) ascertaining and (b) testing a resolution of an ultrasonic testing system, comprising:
- at least one of (a) testing detectability of at least one flaw in a component and (b) evaluating ultrasonic signals of the flaw, including:
- generating an electronic specification of the flaw, the electronic specification including at least one of (a) a two-dimensional and (b) a three-dimensional point pattern;
- after the generating, manufacturing a test specimen, for each point of the point pattern, a microcrack in the test specimen generated at a corresponding position to form a microcrack field representing the flaw; and
- recording by the testing system and evaluating ultrasonic signals of the test specimen.

9. A device for at least one of (a) testing detectability of at least one flaw in a component and (b) evaluating an ultrasonic signal of the flaw, comprising:
- a device adapted to generate an electronic specification of the flaw, the specification including at least one of (a) a two-dimensional and (b) a three-dimensional point pattern;
- a device adapted to produce a test specimen after generation of the electronic specification of the flaw, for each point of the point pattern, a microcrack produced at a position of the point to form a microcrack field representing the flaw; and
- a device adapted to record and evaluate ultrasonic signals of the test specimen.

10. The device according to claim 9, wherein the device adapted to produce the test specimen is adapted to produce the test specimen such that a largest dimension of the microcracks is smaller than wavelength used to record the ultrasonic signals.

11. The device according to claim 9, wherein the device adapted to produce the test specimen includes a laser apparatus adapted to produce microcracks by internal engraving.

12. A method, comprising:
- at least one of (a) ascertaining and (b) testing a resolution of an ultrasonic testing system by a device adapted to at least one of (a) test a detectability of at least one flaw in a component and (b) evaluate an ultrasonic signal of the flaw, the device including:
  - a device adapted to generate an electronic specification of the flaw, the specification including at least one of (a) a two-dimensional and (b) a three-dimensional point pattern;
  - a device adapted to produce a test specimen after generation of the electronic specification of the flaw, for each point of the point pattern, a microcrack produced at a position of the point to form a microcrack field representing the flaw; and
  - a device adapted to record and evaluate ultrasonic signals of the test specimen, the testing system arranged as a part of the device adapted to record and evaluate the ultrasonic signals.

13. A test specimen for calibration of an ultrasonic testing system for at least one of (a) testing a component and (b) evaluating ultrasonic signals of a flaw, the test specimen including microcracks having positions predefined by an electronic specification having at least one of (a) a two-dimensional and (b) a three-dimensional point pattern that corresponds to the flaw.

14. The test specimen according to claim 13, wherein a largest dimension of the microcracks is smaller than a wavelength for an ultrasonic test to be calibrated.

15. The test specimen according to claim 13, wherein the test specimen is formed of a material transparent to visible light.

16. The test specimen according to claim 15, wherein the transparent material includes at least one of (a) crown glass, (b) optical glass, (c) borosilicate glass and (d) quartz glass.

17. The test specimen according to claim 13, wherein the test specimen is formed of a material having approximately same elastic parameters as a material of the component.

* * * * *